(12) United States Patent
Geng et al.

(10) Patent No.: US 10,801,984 B2
(45) Date of Patent: Oct. 13, 2020

(54) CHIP SUBSTRATE, MANUFACTURING METHOD THEREOF, AND GENE SEQUENCING CHIP AND METHOD

(71) Applicants: BOE TECHNOLOGY GROUP CO., LTD., Beijing (CN); BEIJING BOE OPTOELECTRONICS TECHNOLOGY CO., LTD., Beijing (CN)

(72) Inventors: Yue Geng, Beijing (CN); Fengchun Pang, Beijing (CN); Peizhi Cai, Beijing (CN); Le Gu, Beijing (CN)

(73) Assignees: BEIJING BOE OPTOELECTRONICS TECHNOLOGY CO., LTD., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 274 days.

(21) Appl. No.: 16/070,396

(22) PCT Filed: Dec. 14, 2017

(86) PCT No.: PCT/CN2017/116049
§ 371 (c)(1),
(2) Date: Jul. 16, 2018

(87) PCT Pub. No.: WO2018/205602
PCT Pub. Date: Nov. 15, 2018

(65) Prior Publication Data
US 2019/0277790 A1     Sep. 12, 2019

(30) Foreign Application Priority Data

May 11, 2017 (CN) .......................... 2017 1 0330831

(51) Int. Cl.
*G01N 27/22* (2006.01)
*C12Q 1/6874* (2018.01)
(Continued)

(52) U.S. Cl.
CPC ......... *G01N 27/221* (2013.01); *C12Q 1/6825* (2013.01); *C12Q 1/6874* (2013.01);
(Continued)

(58) Field of Classification Search
CPC .. G01N 27/221; G01N 27/225; G01N 27/226; G01N 27/227; G01N 27/3276;
(Continued)

(56) References Cited

U.S. PATENT DOCUMENTS 6,864,692 B1 * 3/2005 Patel .................... G01N 27/227
324/661
7,038,470 B1 * 5/2006 Johnson ............... G01N 27/226
250/390.05
(Continued)

FOREIGN PATENT DOCUMENTS

CN     101454659 A     6/2009
CN     104350162 A     2/2015
(Continued)

OTHER PUBLICATIONS

T. J. Plum, V. Saxena and R. J. Jessing, "Design of a MEMS capacitive chemical sensor based on polymer swelling," 2006 IEEE Workshop on Microelectronics and Electron Devices, 2006. WMED '06., Boise, ID, 2006 (Year: 2006).*
(Continued)

*Primary Examiner* — Daniel R Miller
(74) *Attorney, Agent, or Firm* — Dilworth & Barrese, LLP.; Michael J. Musella, Esq.

(57) ABSTRACT

A chip substrate, a manufacturing method thereof, a gene sequencing chip, and a gene sequencing method. The chip
(Continued)

substrate includes a base substrate; first electrode, located on the base substrate in an array; an insulating layer, located at gaps between two adjacent ones of the first electrodes, and partially covering the two adjacent ones of the first electrodes to form containing spaces being in one-to-one correspondence with the first electrodes; a capacitive dielectric layer, located on a side of the first electrodes away from the base substrate, and located in the containing spaces; and second electrodes, located on a side of the capacitive dielectric layer away from the base substrate, the capacitive dielectric layer includes a first region and a second region, an orthographic projection of the second electrodes on the base substrate is overlapped with an orthographic projection of the first region on the base substrate.

17 Claims, 6 Drawing Sheets

(51) Int. Cl.
  *G01N 27/327* (2006.01)
  *G01N 33/487* (2006.01)
  *G01N 15/10* (2006.01)
  *C12Q 1/6825* (2018.01)
  *G01N 27/74* (2006.01)

(52) U.S. Cl.
  CPC ....... *G01N 15/1031* (2013.01); *G01N 27/225* (2013.01); *G01N 27/226* (2013.01); *G01N 27/227* (2013.01); *G01N 27/3276* (2013.01); *G01N 27/745* (2013.01); *G01N 33/48721* (2013.01)

(58) Field of Classification Search
  CPC .......... G01N 33/48721; G01N 27/745; G01N 15/1031; C12Q 1/6874; C12Q 1/6825
  See application file for complete search history.

(56) References Cited

U.S. PATENT DOCUMENTS

| 2002/0005580 | A1* | 1/2002 | Goodman .......... G01N 33/0031 257/734 |
| 2009/0267057 | A1 | 10/2009 | Setayesh et al. |
| 2014/0034497 | A1 | 2/2014 | Davis et al. |
| 2016/0302729 | A1* | 10/2016 | Starr .................... A61B 5/6852 |

FOREIGN PATENT DOCUMENTS

| CN | 105543071 A | 5/2016 |
| CN | 106497774 A | 3/2017 |
| CN | 107164466 A | 9/2017 |

OTHER PUBLICATIONS

Strong, Z.A., Wang, A.W. & McConaghy, C.F. Hydrogel-Actuated Capacitive Transducer for Wireless Biosensors. Biomedical Microdevices 4, 97-103, 2002 (Year: 2002).*
International Search Report dated Mar. 14, 2018.

* cited by examiner

CHIP SUBSTRATE, MANUFACTURING METHOD THEREOF, AND GENE SEQUENCING CHIP AND METHOD

The present application claims priority of Chinese Patent application No. 201710330831.9 filed on May 11, 2017, the content of which is incorporated in its entirety as portion of the present application by reference herein.

TECHNICAL FIELD

Embodiments of the present disclosure relate to a chip substrate, a manufacturing method thereof, a gene sequencing method, and a gene sequencing method.

BACKGROUND

Gene sequencing technology is the most commonly used technology in modern molecular biology research. Since the first generation of gene sequencing in 1977, gene sequencing technology has achieved considerable development, mainly including the first-generation sanger sequencing technology, the second-generation high-throughput sequencing technology, the third-generation single molecule sequencing technology, and the fourth-generation nanopore sequencing technology.

SUMMARY

At least one embodiment of the present disclosure provides a chip substrate, which includes: a base substrate; first electrodes, located on the base substrate in an array; an insulating layer, located at gaps between two adjacent ones of the first electrodes, and partially covering the two adjacent ones of the first electrodes to form containing spaces being in one-to-one correspondence with the first electrodes; a capacitive dielectric layer, located on a side of the first electrodes away from the base substrate, and located in the containing spaces; and second electrodes, located on a side of the capacitive dielectric layer away from the base substrate, the capacitive dielectric layer (4) includes a first region and a second region, an orthographic projection of the second electrodes on the base substrate is overlapped with an orthographic projection of the first region on the base substrate, the second region is configured to perform a test reaction.

For example, the chip substrate provided by an embodiment of the present disclosure further includes testing points, located on a side of the capacitive dielectric layer away from the base substrate, the insulating layer includes lead holes, and the testing points are electrically connected with the first electrodes through the lead holes.

For example, the chip substrate provided by an embodiment of the present disclosure further includes: magnetic beads, disposed on a side of the capacitive dielectric layer away from the base substrate, and located in the second region, the magnetic beads are in contact with the capacitive dielectric layer, and configured to receive a sample containing DNA.

For example, in the chip substrate provided by an embodiment of the present disclosure, the capacitive dielectric layer includes a pH sensitive hydrogel material.

For example, the chip substrate provided by an embodiment of the present disclosure further includes a protection layer, disposed between the second electrodes and the capacitive dielectric layer, an orthographic projection of the protection layer on the base substrate is overlapped with an orthographic projection of the insulating layer and the second electrodes on the base substrate.

For example, in the chip substrate provided by an embodiment of the present disclosure, the protection layer includes a flexible polymer material.

At least one embodiment of the present disclosure provides a gene sequencing chip, which includes: a chip substrate and an opposed substrate which are cell-assembled, the chip substrate is any one of abovementioned chip substrates.

For example, in the gene sequencing chip provided by an embodiment of the present disclosure, the opposed substrate is provided with a sample inlet and a sample outlet.

For example, in the gene sequencing chip provided by an embodiment of the present disclosure, a flow passageway sidewall layer is provided between the opposed substrate and the chip substrate at a periphery of the gene sequencing chip; the flow passageway sidewall layer, the opposed substrate, and the second electrodes together form a flow passageway used for storing a sequencing reagent.

For example, in the gene sequencing chip provided by an embodiment of the present disclosure, the flow passageway sidewall layer is made of any one selected from the group consisting of silicon oxide, silicon nitride, and polymer material.

For example, in the gene sequencing chip provided by an embodiment of the present disclosure, the opposed substrate is made of any one selected from the group consisting of glass, silicon, and polymer material.

At least one embodiment of the present disclosure provides a manufacturing method of a chip substrate, which includes: forming first electrodes on a base substrate in an array; forming an insulating layer on a side of the first electrodes away from the base substrate, wherein the insulating layer is disposed at gaps between two adjacent ones of the first electrodes, and partially covers the two adjacent ones of the first electrodes to form containing spaces being in one-to-one correspondence with the first electrodes; forming a capacitive dielectric layer on a side of the first electrodes away from the base substrate, the capacitive dielectric layer being located in the containing spaces; and forming second electrodes on a side of the capacitive dielectric layer away from the base substrate, the capacitive dielectric layer includes a first region and a second region, an orthographic projection of the second electrodes on the base substrate is overlapped with an orthographic projection of the first region on the base substrate, the second region is configured to perform a test reaction.

For example, the manufacturing method of the chip substrate provided by an embodiment of the present disclosure further includes: forming lead holes in the insulating layer to expose a part of the first electrodes; and forming testing points on a side of the capacitive dielectric layer away from the base substrate, the testing points are electrically connected with the first electrodes through the lead holes.

For example, the manufacturing method of the chip substrate provided by an embodiment of the present disclosure further includes: disposing magnetic beads on a side of the capacitive dielectric layer away from the base substrate, the magnetic beads being located in the second region, the magnetic beads are in contact with the capacitive dielectric layer, and configured to receive a sample containing DNA.

For example, in the manufacturing method of the chip substrate provided by an embodiment of the present disclosure, forming the lead holes in the insulating layer to expose the part of the first electrodes, the manufacturing method further includes: forming a protection layer on a side of the insulating layer and the capacitive dielectric layer away from the base substrate.

For example, in the manufacturing method of the chip substrate provided by an embodiment of the present disclosure, forming the lead holes in the insulating layer to expose the part of the first electrodes includes: forming the lead holes sequentially running through the protection layer and the insulating layer and exposing the part of the first electrodes in the protection layer and the insulating layer.

An embodiment of the disclosure provides a gene sequencing method of the chip substrate as mentioned above includes: acquiring a first distance between a second electrode and a first electrode which are correspondingly disposed and a first dielectric constant of the capacitive dielectric layer; acquiring a first capacitive value of the second electrode and the first electrode which are correspondingly disposed according to the first distance and the first dielectric constant; performing a gene test reaction in the second region and acquiring a second distance between the second electrode and the first electrode and a second dielectric constant of the capacitive dielectric layer; acquiring a second capacitive value of the second substrate and the first electrode which are correspondingly disposed according to the second distance and the second dielectric constant; and acquiring a gene segment sequence corresponding to the second electrode and the first electrode which are correspondingly disposed by utilizing a difference between the second capacitive value and the first capacitive value.

BRIEF DESCRIPTION OF THE DRAWINGS

In order to clearly illustrate the technical solution of embodiments of the present disclosure, the drawings of the embodiments will be briefly described in the following, it is obvious that the drawings in the description are only related to some embodiments of the present disclosure and not limited to the present disclosure.

REFERENCE SIGNS

Figure 1:
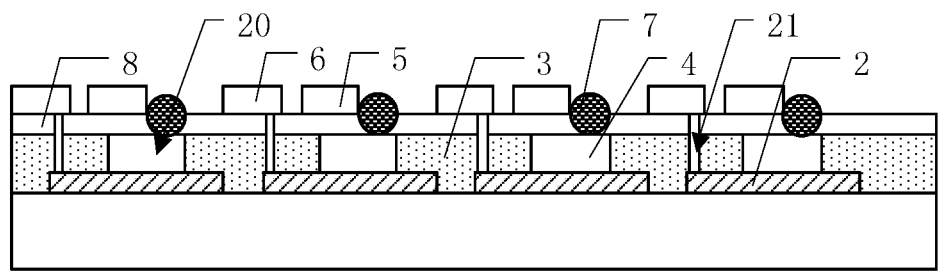
FIG. 1 is a schematic structural diagram of a chip substrate according to an embodiment of the present disclosure.

1—base substrate; 2—first electrode; 3—insulating layer; 4—capacitive dielectric layer; 5—second electrode; 6—testing point; 7—magnetic bead; 8—protection layer; 9—opposed substrate; 10—sample inlet; 11—sample outlet; 12—flow passageway sidewall layer; 13—flow passageway; 20—containing space; 21—lead hole.

DETAILED DESCRIPTION

In order to make objects, technical details and advantages of the embodiments of the disclosure apparent, the technical solutions of the embodiments will be described in a clearly and fully understandable way in connection with the drawings related to the embodiments of the disclosure. Apparently, the described embodiments are just a part but not all of the embodiments of the disclosure. Based on the described embodiments herein, those skilled in the art can obtain other embodiment(s), without any inventive work, which should be within the scope of the disclosure.

Unless otherwise defined, all the technical and scientific terms used herein have the same meanings as commonly understood by one of ordinary skill in the art to which the present disclosure belongs. The terms "first," "second," etc., which are used in the present disclosure, are not intended to indicate any sequence, amount or importance, but distinguish various components. Also, the terms "comprise," "comprising," "include," "including," etc., are intended to specify that the elements or the objects stated before these terms encompass the elements or the objects and equivalents thereof listed after these terms, but do not preclude the other elements or objects. The phrases "connect", "connected", etc., are not intended to define a physical connection or mechanical connection, but may include an electrical connection, directly or indirectly.

A common gene sequencing method generally adopts a fluorescence test method, and major sequencing companies such as Illumina, Roche 454, and ABI all adopt the fluorescence test method for gene sequencing. The fluorescence test method performs modifications with different fluorescence groups to different species of bases, upon these bases being paired with a gene segment to be tested, the fluorescence groups will be released, and the fluorescence test method can determine a specie of the base by detecting a color of fluorescent light through an optical system, and finally obtain a sequence of the gene segment to be tested.

Although the abovementioned gene sequencing method has a visualized test result and high sequencing accuracy. However, the abovementioned gene sequencing method needs to perform fluorescent labeling of different colors to four species of bases, and thousands of rounds of base pairing are required during the sequencing process, thus, a large amount of test reagents are required, resulting in a substantial increase in the costs of the test reagents. It is not conducive to the popularization and promotion of gene sequencing in medicine and other fields.

Embodiments of the present disclosure provide a chip substrate, a manufacturing method thereof, a gene sequencing chip, and a gene sequencing method. The chip substrate includes a base substrate; first electrodes, located on the base substrate in an array; an insulating layer, located at gaps between two adjacent ones of the first electrodes, and partially covering the two adjacent ones of the first electrodes to form containing spaces being in one-to-one correspondence with the first electrodes; a capacitive dielectric layer, located on a side of the first electrodes away from the base substrate, and located in the containing spaces; and second electrodes, located on a side of the capacitive dielectric layer away from the base substrate, the capacitive dielectric layer includes a first region and a second region, an orthographic projection of the second electrodes on the base substrate is overlapped with an orthographic projection of the first region on the base substrate, the second region is configured to perform a test reaction. Through the abovementioned chip substrate, by performing a test reaction in the second region, for example, a base pairing reaction, the hydrogen ions generated by the base pairing reaction enter the capacitive dielectric layer, causing the capacitive dielectric layer to swell, resulting in changes of a distance between the first electrode and the second electrode and the dielectric constant of the capacitive dielectric layer. And finally, the capacitive value between the first electrode and the second electrode which are correspondingly disposed changes. By means of continuously monitoring the change of the abovementioned capacitive value, a gene segment sequence can be finally obtained. Thus, the chip substrate can transform a chemical signal during a sequencing process into an electrical signal, without performing a special labeling such as a fluorescent probe to various kinds of bases, thereby having relatively low costs. In addition, the abovementioned chip substrate has a simple structure and a low degree of process complexity, and thus can be manufactured by using a usual lithography process, which is conducive to the popularization and promotion of gene sequencing in medicine and other fields.

Figure 2:
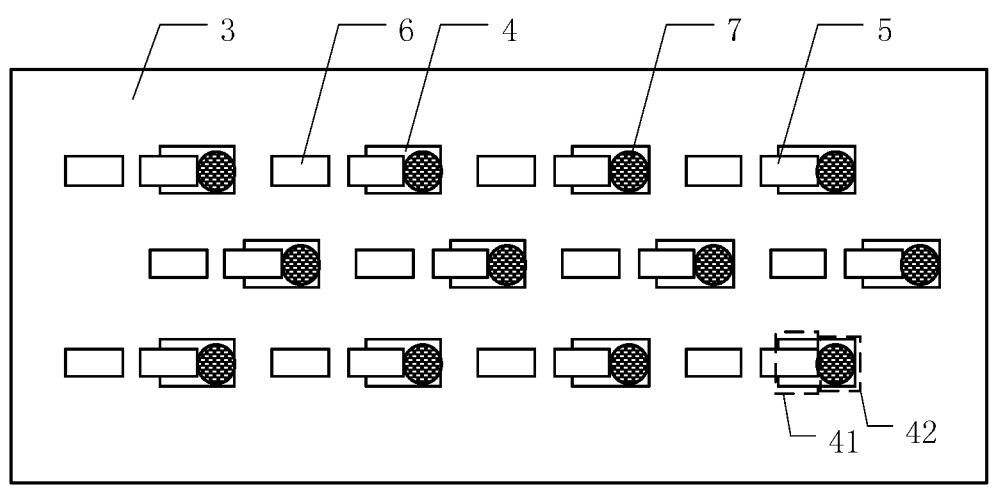
FIG. 2 is a top view of a prepared chip substrate according to an embodiment of the present disclosure.

An embodiment of the present disclosure provides a structure of a chip substrate. FIG. 1 is a schematic structural diagram of a chip substrate according to an embodiment of the present disclosure. FIG. 2 is a top view of a prepared chip substrate according to an embodiment of the present disclosure. As illustrated by FIG. 1 and FIG. 2, the chip substrate includes: a base substrate 1; first electrodes 2, i.e., lower plate electrodes, disposed on the base substrate 1 in an array; and an insulating layer 3 disposed at gaps between two adjacent ones of the first electrodes 2, and partially covering the two adjacent ones of the first electrodes 2 to form containing spaces 20 being in one-to-one correspondence with the first electrodes 2; a capacitive dielectric layer 4, located on a side of the first electrodes 2 away from the base substrate 1, and located in the containing spaces 20; and second electrodes 5, i.e., upper plate electrodes, located on a side of the capacitive dielectric layer 4 away from the base substrate 1, the capacitive dielectric layer 4 includes a first region 41 and a second region 42, an orthographic projection of the second electrodes 5 on the base substrate 1 is overlapped with an orthographic projection of the first region 41 on the base substrate 1, the second region 42 is configured to perform a test reaction.

In the chip substrate provided in the present embodiment, a first electrode and a second electrode which are correspondingly disposed, and a capacitive dielectric layer disposed between the first electrode and the second electrode can form a capacitor; upon a test reaction, for example, a test reaction such as a base pairing reaction, occurring in the second region, ions generated by the test reaction, such as hydrogen ions, enters the capacitive dielectric layer, causing the capacitive dielectric layer to swell, resulting in changes of a distance between the first electrode and the second electrode and a dielectric constant of the dielectric layer. And finally, a capacitance value between the first electrode and the second electrode which are correspondingly disposed changes, so that it can be determined whether the test reaction occurred or not. In addition, by means of continuously monitoring a change of the abovementioned capacitive value, a gene segment sequence can be obtained.

For example, in some examples, as illustrated by FIGS. 1 and 2, the chip substrate further includes a test point 6 located on a side of the capacitive dielectric layer 4 away from the base substrate 1, and the insulating layer 3 includes a lead hole 21, and a test point is electrically connected with the first electrode 2 through the lead hole 21. Thus, by means of detecting a capacitive value of the test point and the second electrode, it can be determined that whether the test reaction occurred or not.

For example, in some examples, as illustrated by FIGS. 1 and 2, the chip substrate further includes a magnetic bead 7 disposed on a side of the capacitive dielectric layer 4 away from the base substrate 1, and located in a second region 42. The magnetic bead 7 is in contact with the capacitive dielectric layer 4 and is configured to receive a sample containing DNA. Thus, the sample containing DNA can be immobilized on the magnetic bead, and then different bases can be sequentially introduced; by means of determining whether a base pairing reaction occurred or not, a gene sequencing of the sample containing DNA can be achieved.

For example, in some examples, the first electrodes 2 disposed in an array can be formed by depositing a metal film on the base substrate 1, and etching the metal film. A forming mode of the first electrodes 2 will be described below. The detailed description in the present embodiment is omitted here.

For example, in some examples, the insulating layer 3 can be formed through a patterning process. A material of the insulating layer 3 is usually a material such as silicon oxide or silicon nitride. The specific material for forming the insulating layer 3 is not limited by the embodiment of the present disclosure.

For example, in some examples, the capacitive dielectric layer 4 can include a pH sensitive hydrogel material. Upon the pH sensitive hydrogel material encountering hydrogen ions, a swelling phenomenon occurs, further resulting in the distance between the second electrode 5 and the first electrode 2 increases, which can cause the dielectric constant between the second electrode 5 and the first electrode 2 to change. And finally, the capacitive value of the chip substrate changes.

It can be understood that the capacitive dielectric layer 4 in the embodiment of the present disclosure can be made of other materials which can swell upon encountering hydrogen ions, and the specific material for forming the capacitive dielectric layer 4 is not limited by the embodiments of the present disclosure.

For example, in some examples, the second electrode 5 and the test point 6 can be formed through a patterning process, the second electrode 5 partially covers the capacitive dielectric layer 4, and the test point 6 is connected with the first electrode 2 through a lead hole running through the insulating layer 3.

In the embodiments of the present disclosure, each of the second electrodes 5 can be provided with one or more test points 6, which is not limited in the present embodiment of the disclosure.

For example, in some examples, the test point 6 may be communicated with the first electrode 2. By means of detecting a capacitance between the test point 6 and the second electrode 5, the capacitance between the second electrode 5 and the first electrode 2 can also be known, and gene sequencing can be achieved.

For example, in some examples, the magnetic bead 7 is disposed in a region of the capacitive dielectric layer 4 which is not covered by the second electrode 5, i.e., the second region 42, and is in contact with the capacitive dielectric layer 4. The magnetic bead 7 can be used to receive a sample containing DNA. The magnetic bead 7 and the second electrode 5 can fitly cover the capacitive dielectric layer 4 and the insulating layer.

Upon performing gene sequencing, DNA on the sample containing DNA received by the magnetic beads 7 undergoes a sequencing reaction to generate hydrogen ions, and the hydrogen ions enter the capacitive dielectric layer 4 and cause the capacitive dielectric layer 4 to swell, so that a distance between the electrode 5 and the first electrode 2 can be changed, and a dielectric constant of the capacitive dielectric layer 4 can also be changed, thereby resulting a change of a capacitance value of the chip substrate, so as to determine a corresponding gene segment sequence.

For example, the chip substrate in the embodiment of the present disclosure can further include a protection layer 8, which is formed between the second electrode 5 and the capacitive dielectric layer 4 and covers the insulating layer 3 and the capacitive dielectric layer 4. The protection layer 8 can protect the capacitive dielectric layer 4 from being eroded by various etching liquids during an etching process. For a good contact of the capacitive dielectric layer 4 and the second electrode 5, the protection layer 8 can be made of a flexible polymer, but the specific material for forming the protection layer 8 is not limited in the embodiments of the present disclosure.

Figure 3:
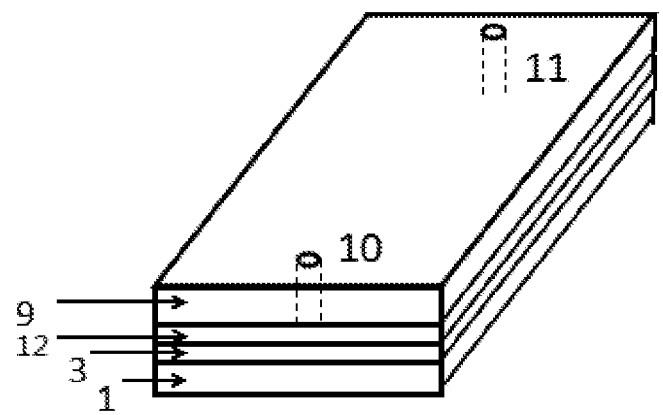
FIG. 3 is a schematic structural diagram of a gene sequencing chip according to an embodiment of the present disclosure.
Figure 4:
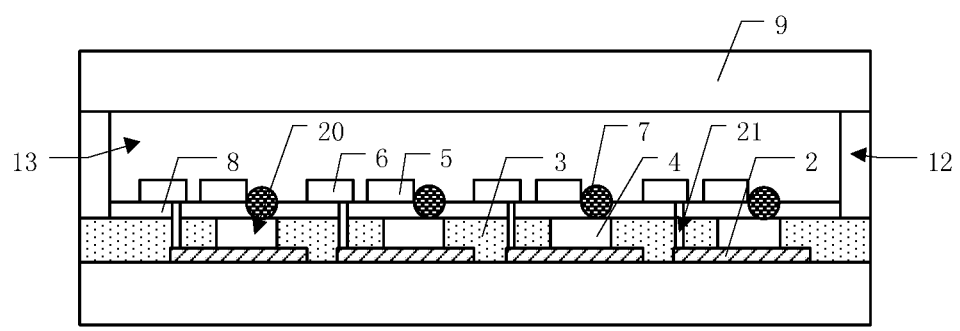
FIG. 4 is a schematic structural diagram of a cross section of a gene sequencing chip according to an embodiment of the present disclosure.

In the present embodiment, the magnetic bead is in contact with the capacitive dielectric layer. For a gene sequencing process, the magnetic bead receives a sample containing DNA. During the gene sequencing process, hydrogen ions generated by the sequencing reaction of DNA enter the capacitive dielectric layer, cause the capacitive dielectric layer to swell, resulting in a change of a distance between the plates of the capacitor and the dielectric constant of the dielectric layer, which ultimately results in a change of the capacitance of the chip substrate. By means of continuously monitoring the change of the capacitance value of each sequencing cell in each sequencing process, and a final gene segment sequence can be obtained, this method transforms a chemical signal in the sequencing process into an electrical signal, without performing a special labeling such as a fluorescent probe to various kinds of bases, thereby having relatively low costs. The chip substrate has a simple structure and a low degree of process complexity, which is the same with a usual lithography process, and is conducive to the popularization and promotion of gene sequencing in medicine and other fields An embodiment of the present disclosure further provides a gene sequencing chip. FIG. 3 is a schematic structural diagram of a gene sequencing chip according to an embodiment of the present disclosure. FIG. 4 is a schematic structural diagram of a cross section of a gene sequencing chip according to an embodiment of the present disclosure. As illustrated by FIGS. 3 and 4, the gene sequencing chip can include an opposed substrate 9 and the chip substrate described in any examples of the abovementioned embodiments, and the opposed substrate 9 and the chip substrate are cell-assembled (bonded with each other). Thus, by using the gene sequencing chip, a sample to be tested can be placed in the second region, different species of bases can be introduced, upon base pairing reactions occurring in the second region, hydrogen ions generated by the base pairing reactions enter the capacitive dielectric layer, causing the capacitive dielectric layer to swell, thereby resulting in changes of a distance between the first electrode and the second electrode and a dielectric constant of the capacitive dielectric layer. And finally a capacitive value between the first electrode and the second electrode which are correspondingly disposed changes, so that it can be determined that whether the reaction occurred or not. In addition, by means of continuously monitoring the change of the capacitive value between the first electrode and the second electrode, a gene segment sequence can be obtained.

For example, the opposed substrate 9 is provided with a sample inlet 10 and a sample outlet 11.

In the embodiments of the present disclosure, the opposed substrate 9 corresponding to the second electrode 5 is provided with the sample inlet 10 and the sample outlet 11, the sample inlet 10 can be used for providing a sample containing DNA to the magnetic bead 7 during gene sequencing, and the sample outlet 11 can be used for discharging the used sequencing reagent through the outlet 11 after the gene sequencing is completed.

For example, a flow passageway sidewall layer 12 is provided between the opposed substrate 9 and the substrate 1 at the periphery of the gene sequencing chip, the flow passageway sidewall layer 12, the opposed substrate 9, and the second electrode 5 together form a flow passageway 13 used for storing a sequencing reagent.

For example, the flow passageway sidewall layer 12 can be made of any one material selected from the group consisting of silicon oxide, silicon nitride, a polymer material, and the like, and the opposed substrate 9 can be made of any one material selected from the group consisting of glass, silicon, a polymer material, and the like.

It should be noted that, in practical applications, those skilled in the art can select materials for forming the flow passageway sidewall layer 12 and the opposed substrate 9 according to actual needs, and the embodiments of the present disclosure are not limited thereto.

In addition to the beneficial effects of the chip substrate provided by the first embodiment, the gene sequencing chip according to the present embodiment of the present disclosure can be further provided with a flow passageway sidewall layer to serve as a retaining wall of the chip substrate, which can better protect the chip substrate. Moreover, the flow passageway surrounded by the flow passageway sidewall layer, the opposed substrate, and the second electrode can be convenient for storing the sequencing reagent, thereby saving an extra space for independently storing the sequencing reagent.

Figure 5:
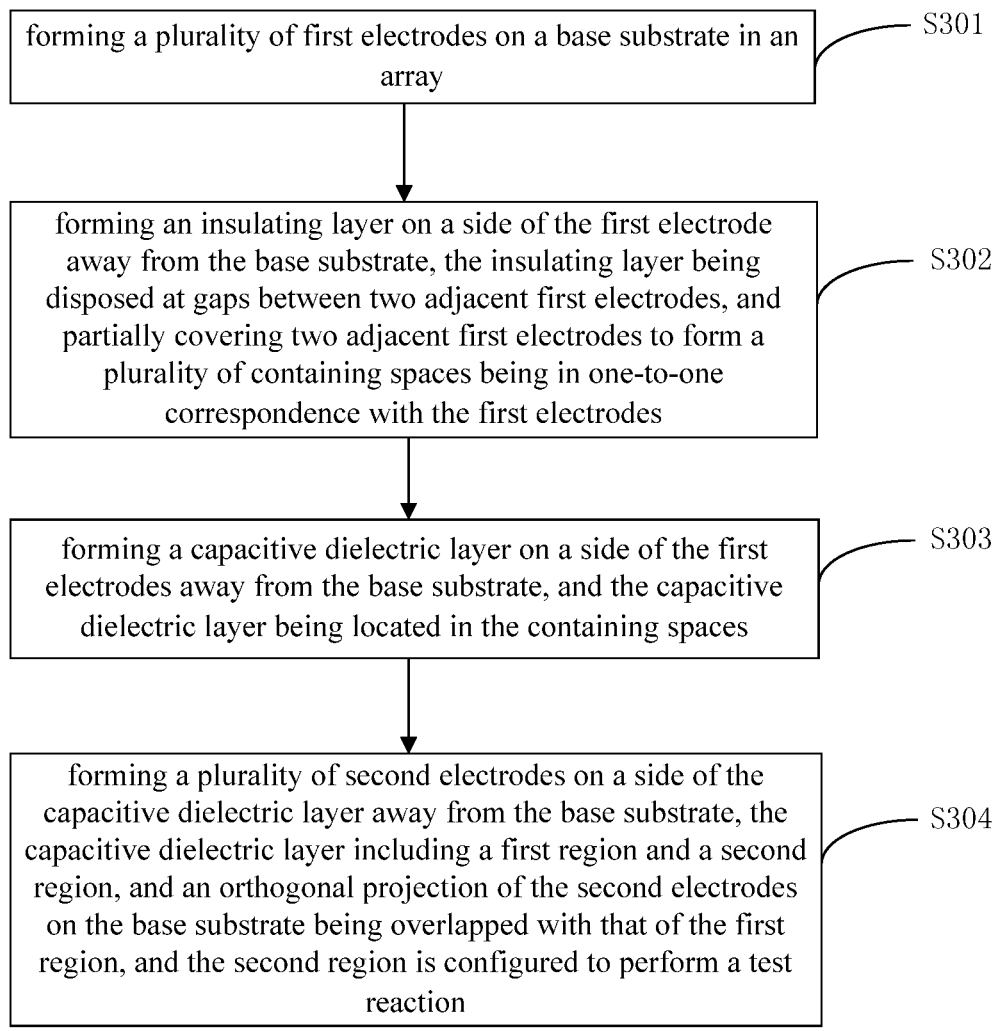
FIG. 5 is a flow diagram of a manufacturing method of a chip substrate according to an embodiment of the present disclosure.

An embodiment of the present disclosure further provides a manufacturing method of a chip substrate. FIG. 5 is a flow diagram of a manufacturing method of a chip substrate according to an embodiment of the present disclosure. As illustrated by FIG. 5, the manufacturing method the chip substrate includes the following steps:

Step S301: forming first electrodes on a base substrate in an array.

Figure 5A:
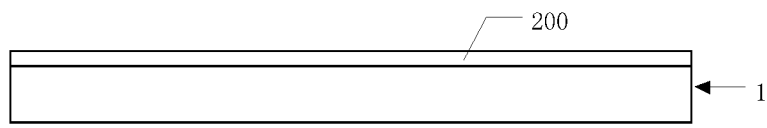
FIG. 5a is a schematic structural diagram of a manufacturing process of a chip substrate according to an embodiment of the present disclosure.
Figure 5B:
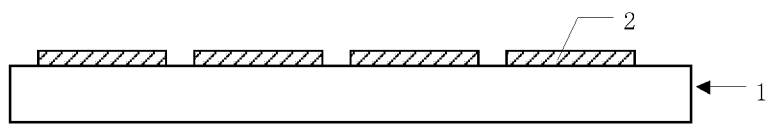
FIG. 5b is a schematic structural diagram of another manufacturing process of a chip substrate according to an embodiment of the present disclosure.

For example, a patterning process can be used to form the first electrodes on the base substrate in an array. For example, as illustrated by FIG. 5a, firstly a metal film 200 is deposited on the base substrate 1, and then, as illustrated by FIG. 5b, the deposited metal film 200 is etched by a photolithography process to form the first electrodes 2 in an array. It can be understood that the abovementioned examples are merely examples for better understanding of the technical solutions of the embodiments of the present disclosure and are not to be regarded as the sole limitation of the embodiments of the present disclosure.

Step S302: forming an insulating layer on a side of the first electrode away from the base substrate, the insulating layer being disposed at gaps between two adjacent first electrodes, and partially covers two adjacent first electrodes to form containing spaces being in one-to-one correspondence with the first electrodes.

Step S303: forming a capacitive dielectric layer on a side of the first electrodes away from the base substrate, and the capacitive dielectric layer being located in the containing spaces.

Step S304: forming second electrodes on a side of the capacitive dielectric layer away from the base substrate, the capacitive dielectric layer including a first region and a second region, and an orthogonal projection of the second electrodes on the base substrate being overlapped with that of the first region, and the second region is configured to perform a test reaction.

Figure 5C:
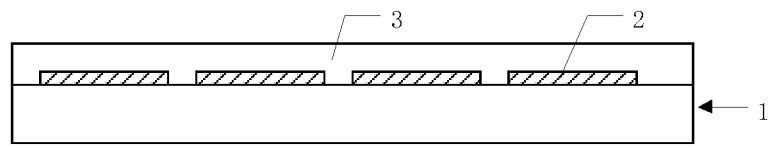
FIG. 5c is a schematic structural diagram of another manufacturing process of a chip substrate according to an embodiment of the present disclosure.
Figure 5D:
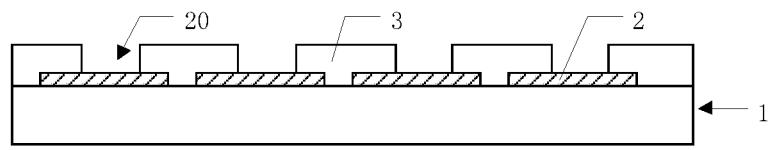
FIG. 5d is a schematic structural diagram of another manufacturing process of a chip substrate according to an embodiment of the present disclosure.
Figure 5E:
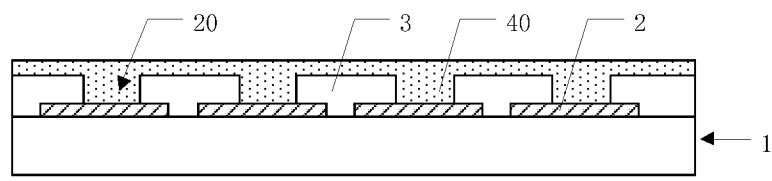
FIG. 5e is a schematic structural diagram of another manufacturing process of a chip substrate according to an embodiment of the present disclosure.
Figure 5F:
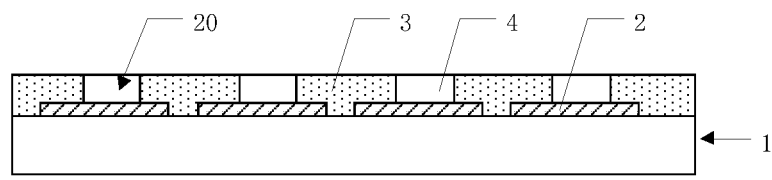
FIG. 5f is a schematic structural diagram of another manufacturing process of a chip substrate according to an embodiment of the present disclosure.

In the embodiment of the present disclosure, the abovementioned step S302, step S303, and step S304 can, as illustrated by FIG. 5c, an insulating layer 3 is deposited on the first electrodes 2 and the base substrate 1, then, as illustrated by FIG. 5d, the insulating layer 3 is etched to form containing spaces 20 for depositing a capacitive dielectric layer by a photolithography process, then, as illustrated by FIG. 5e, a capacitive dielectric layer 4 is deposited in the containing spaces 20, and further, as illustrated by FIG. 5f, the capacitive dielectric layer 4 is etched so that an upper surface of the capacitive dielectric layer 4 is flush with an upper surface of the insulating layer 3. Then, second electrodes 5 is formed on the side of the capacitive dielectric layer 4 away from the base substrate 1.

For example, in some examples, the manufacturing method of a chip substrate according to an embodiment of the present disclosure further includes: forming lead holes in the insulating layer, each of the lead holes exposing a part of a corresponding one of the first electrodes; and forming test points on a side of the capacitive dielectric layer away from the base substrate. The test points are electrically connected with the first electrodes through the lead holes.

Figure 5G:
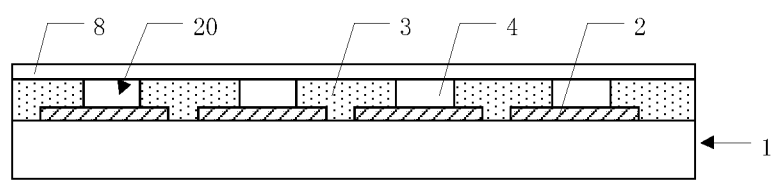
FIG. 5g is a schematic structural diagram of another manufacturing process of a chip substrate according to an embodiment of the present disclosure.

For example, as illustrated by FIG. 5g, the insulating layer 3 is etched to form the lead holes 21 running through the insulating layer 3 and used for the connection of the second electrodes 5 and the first electrodes 2.

For example, in some examples, a manufacturing method of a chip substrate according to an embodiment of the present disclosure further includes: providing a magnetic bead on a side of the capacitive dielectric layer away from the base substrate, the magnetic bead is located in the second region, and the magnetic bead is in contact with capacitive dielectric layer and is configured to receive a sample containing DNA.

Figure 5H:
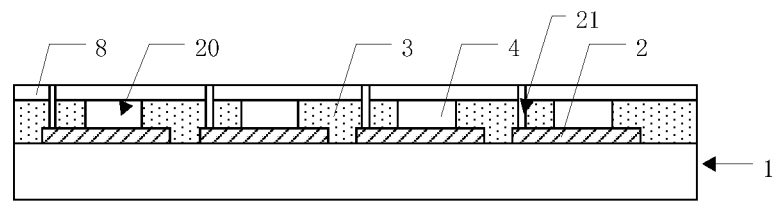
FIG. 5h is a schematic structural diagram of another manufacturing process of a chip substrate according to an embodiment of the present disclosure.
Figure 5I:
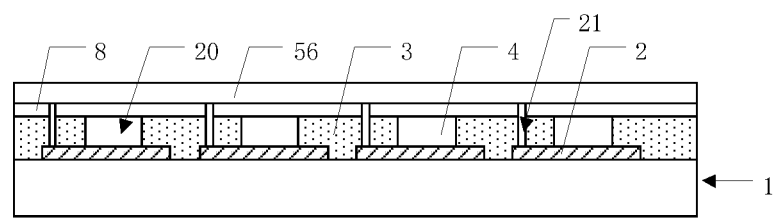
FIG. 5i is a schematic structural diagram of another manufacturing process of a chip substrate according to an embodiment of the present disclosure.
Figure 5J:
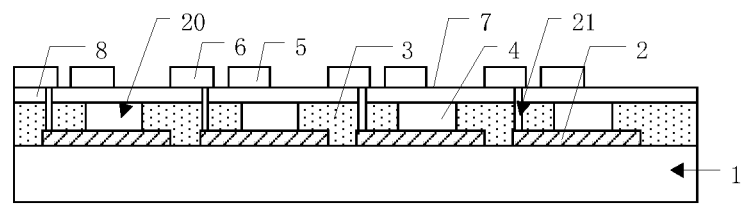
FIG. 5j is a schematic structural diagram of another manufacturing process of a chip substrate according to an embodiment of the present disclosure.
Figure 5K:
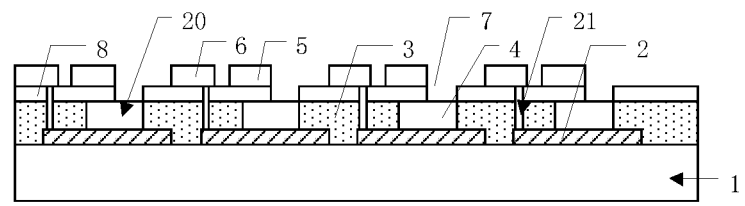
FIG. 5k is a schematic structural diagram of another manufacturing process of a chip substrate according to an embodiment of the present disclosure.

For example, in some examples, as illustrated by FIG. 5i, a metal film 56 is deposited on the chip substrate, and then, as illustrated by FIG. 5j, using a photolithography process, the deposited metal film 56 is etched to form the second electrodes in an array, and test points 6 is formed used for connecting the first electrodes 2.

It can be understood that, the abovementioned examples are merely examples for better understanding of the technical solutions of the embodiments of the present disclosure and are not to be regarded as the sole limitation of the embodiments of the present disclosure.

For example, in some examples, before forming lead holes in the insulating layer to expose a part of a corresponding one of the first electrodes, the manufacturing method further includes: forming a protection layer on a side of the insulating layer and the capacitive dielectric layer away from the base substrate. For example, as illustrated by FIG. 5h, an array protection layer 8 is deposited on the insulating layer 3 and the capacitive dielectric layer 4. The protection layer 8 is deposited between the second electrode 5 and the capacitive dielectric layer 4, and covers the insulating layer 3 and the capacitive dielectric layer 4.

For example, in some examples, the step of forming lead holes in the insulating layer to expose a part of a corresponding one of the first electrodes includes: forming lead holes sequentially running through the protection layer and the insulating layer to expose a part of the first electrodes in the protection layer and the insulating layer.

Figure 6:
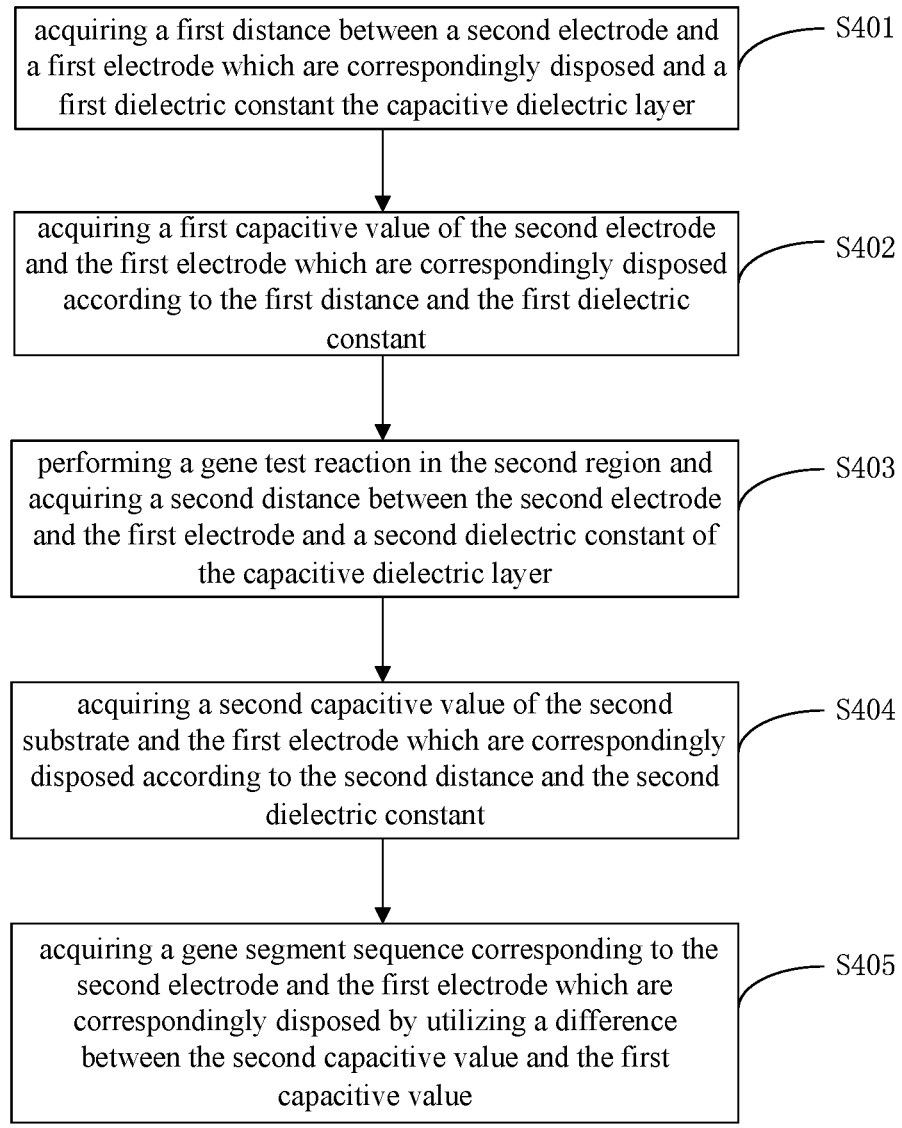
FIG. 6 is a flow diagram of a gene sequencing method according to an embodiment of the present disclosure.

An embodiment of the present disclosure further provides a gene sequencing method. FIG. 6 is a flow diagram of steps of a gene sequencing method according to an embodiment of the present disclosure. The gene sequencing method can use the chip substrate according to any one of the abovementioned examples. As illustrated by FIG. 6, the gene sequencing method includes the following steps:

Step S401: acquiring a first distance between a second electrode and a first electrode which are correspondingly disposed and a first dielectric constant the capacitive dielectric layer.

For example, a capacitive dielectric layer is formed between the second electrode and the first electrode. Before performing gene sequencing, a first distance between the second electrode and the first electrode can be obtained in advance, and a first dielectric constant of the capacitive dielectric layer can be obtained according to a material for forming the capacitive dielectric layer.

Step S402: acquiring a first capacitive value of the second electrode and the first electrode which are correspondingly disposed according to the first distance and the first dielectric constant.

For example, the first capacitance value of a first sequencing unit can be calculated by the first distance and the first dielectric constant.

Step S403: performing a gene test reaction in the second region and acquiring a second distance between the second electrode and the first electrode and a second dielectric constant of the capacitive dielectric layer.

For example, after the first capacitance value is measured, a sample containing DNA and required sequencing reagents are provided to the magnetic bead through a sample inlet on the opposed substrate to perform gene sequencing. During gene sequencing, DNA will undergo DNA sequencing reaction. A sequencing reaction occurs to generate hydrogen ions enter into the capacitive dielectric layer, resulting in swelling of the dielectric layer of the capacitor, which can increase the spacing between the second electrode and the first electrode and also cause a change in the dielectric constant of the dielectric layer of the capacitor.

Step S404: acquiring a second capacitive value of the second substrate and the first electrode which are correspondingly disposed according to the second distance and the second dielectric constant.

For example, the second capacitance value of the first sequencing unit can be calculated by the second distance and the second dielectric constant.

Step S405: acquiring a gene segment sequence corresponding to the second electrode and the first electrode which are correspondingly disposed by utilizing a difference between the second capacitive value and the first capacitive value.

In the chip substrate, a first electrode and a second electrode which are correspondingly disposed, and a capacitive dielectric layer disposed between the first electrode and the second electrode can form a capacitor; upon a test reaction, for example, a test reaction such as a base pairing reaction, occurring in the second region, ions generated by the test reaction, such as hydrogen ions, enter the capacitive dielectric layer, causing the capacitive dielectric layer to swell, resulting in changes of a distance between the first electrode and the second electrode and a dielectric constant of the dielectric layer. And finally, a capacitance value between the first electrode and the second electrode which are correspondingly disposed changes, so that it can be determined whether the test reaction occurred or not. Thus, by means of utilizing a difference between the first capacitive value and the second capacitive value, a gene segment sequence corresponding to the first electrode and the second electrode which are correspondingly disposed can be obtained. It should be noted that, the embodiment of the present disclosure includes but is not limited thereto, and the corresponding first electrodes and second electrodes can also be directly measured to obtain the abovementioned first capacitance value and second capacitance value.

For simplicity, the foregoing embodiments are all described as a series of action combinations, but those skilled in the art should understand that the present disclosure is not limited by the described order of actions, because these steps can be performed in other orders or simultaneously according to the present disclosure. Secondly, those skilled in the art should also understand that the embodiments described in the specification all belong to preferred embodiments, and the involved actions and modules are not certainly necessary for the present disclosure.

The following points should to be explained:

(1) The accompanying drawings involve only the structure(s) in connection with the embodiment(s) of the present disclosure, and other structure(s) can be referred to common design(s).

(2) In the absence of conflict, the features of the same embodiment and the different embodiments ban be combined with each other.

The foregoing is only the embodiments of the present invention and not intended to limit the scope of protection of the present invention, alternations or replacements which can be easily envisaged by any skilled person being familiar with the present technical field shall fall into the protection scope of the present disclosure. Thus, the protection scope of the present disclosure should be based on the protection scope of the claims.

What is claimed is:

1. A chip substrate, comprising:
   a base substrate;
   first electrodes, located on the base substrate in an array;
   an insulating layer, located at gaps between two adjacent ones of the first electrodes, and partially covering the two adjacent ones of the first electrodes to form containing spaces being in one-to-one correspondence with the first electrodes;
   a capacitive dielectric layer, located on a side of the first electrodes away from the base substrate, and located in the containing spaces; and
   second electrodes, located on a side of the capacitive dielectric layer away from the base substrate,
   wherein the capacitive dielectric layer comprises a first region and a second region, an orthographic projection of the second electrodes on the base substrate is overlapped with an orthographic projection of the first region on the base substrate, the second region is configured to perform a test reaction.

2. The chip substrate according to claim 1, further comprising:
   testing points, located on a side of the insulating layer away from the base substrate,
   wherein the insulating layer comprises lead holes, and the testing points are electrically connected with the first electrodes through the lead holes.

3. The chip substrate according to claim 1, further comprising:
   magnetic beads, disposed on a side of the capacitive dielectric layer away from the base substrate, and located in the second region,
   wherein the magnetic beads are in contact with the capacitive dielectric layer, and configured to receive a sample containing DNA.

4. The chip substrate according to claim 1, wherein the capacitive dielectric layer comprises a pH sensitive hydrogel material.

5. The chip substrate according to claim 1, further comprising:
   a protection layer, disposed between the second electrodes and the capacitive dielectric layer,
   wherein an orthographic projection of the protection layer on the base substrate is overlapped with an orthographic projection of the insulating layer and the second electrodes on the base substrate.

6. The chip substrate according to claim 5, wherein the protection layer comprises a flexible polymer material.

7. A gene sequencing chip, comprising:
   a chip substrate and an opposed substrate which are cell-assembled,
   wherein the chip substrate is the chip substrate according to claim 1.

8. The gene sequencing chip according to claim 7, wherein the opposed substrate is provided with a sample inlet and a sample outlet.

9. The gene sequencing chip according to claim 7, wherein a flow passageway sidewall layer is provided between the opposed substrate and the chip substrate at a periphery of the gene sequencing chip; the flow passageway sidewall layer, the opposed substrate, and the second electrodes together form a flow passageway used for storing a sequencing reagent.

10. The gene sequencing chip according to claim 9, wherein the flow passageway sidewall layer is made of any one selected from the group consisting of silicon oxide, silicon nitride, and polymer material.

11. The gene sequencing chip according to claim 7, wherein the opposed substrate is made of any one selected from the group consisting of glass, silicon, and polymer material.

12. A gene sequencing method by using the chip substrate according to claim 1, comprising:
   acquiring a first distance between a second electrode and a first electrode which are correspondingly disposed and a first dielectric constant of the capacitive dielectric layer;
   acquiring a first capacitive value of the second electrode and the first electrode which are correspondingly disposed according to the first distance and the first dielectric constant;
   performing a gene test reaction in the second region and acquiring a second distance between the second electrode and the first electrode and a second dielectric constant of the capacitive dielectric layer;
   acquiring a second capacitive value of the second substrate and the first electrode which are correspondingly disposed according to the second distance and the second dielectric constant; and
   acquiring a gene segment sequence corresponding to the second electrode and the first electrode which are correspondingly disposed by utilizing a difference between the second capacitive value and the first capacitive value.

13. A manufacturing method of a chip substrate, comprising:
   forming first electrodes on a base substrate in an array;
   forming an insulating layer on a side of the first electrodes away from the base substrate, wherein the insulating layer is disposed at gaps between two adjacent ones of the first electrodes, and partially covers the two adjacent ones of the first electrodes to form containing spaces being in one-to-one correspondence with the first electrodes;
   forming a capacitive dielectric layer on a side of the first electrodes away from the base substrate, the capacitive dielectric layer being located in the containing spaces; and
   forming second electrodes on a side of the capacitive dielectric layer away from the base substrate,
   wherein the capacitive dielectric layer comprises a first region and a second region, an orthographic projection of the second electrodes on the base substrate is overlapped with an orthographic projection of the first region on the base substrate, and the second region is configured to perform a test reaction.

14. The manufacturing method of the chip substrate according to claim 13, further comprising:
   forming lead holes in the insulating layer to expose a part of the first electrodes; and
   forming testing points on a side of the insulating layer away from the base substrate,
   wherein the testing points are electrically connected with the first electrodes through the lead holes.

15. The manufacturing method of the chip substrate according to claim 13, further comprising:
   disposing magnetic beads on a side of the capacitive dielectric layer away from the base substrate, the magnetic beads being located in the second region,
   wherein the magnetic beads are in contact with the capacitive dielectric layer, and configured to receive a sample containing DNA.

16. The manufacturing method of the chip substrate according to claim 14, wherein before forming the lead holes in the insulating layer to expose the part of the first electrodes, the manufacturing method further comprises:
   forming a protection layer on a side of the insulating layer and the capacitive dielectric layer away from the base substrate.

17. The manufacturing method of the chip substrate according to claim 16, wherein forming the lead holes in the insulating layer to expose the part of the first electrodes comprises:
   forming the lead holes sequentially running through the protection layer and the insulating layer and exposing the part of the first electrodes in the protection layer and the insulating layer.

* * * * *

UNITED STATES PATENT AND TRADEMARK OFFICE
CERTIFICATE OF CORRECTION

PATENT NO. : 10,801,984 B2  
APPLICATION NO. : 16/070396  
DATED : October 13, 2020  
INVENTOR(S) : Yue Gang Page 1 of 1

It is certified that error appears in the above-identified patent and that said Letters Patent is hereby corrected as shown below:

On the Title Page

(73) Assignees Should read as: BOE TECHNOLOGY GROUP CO., LTD., Beijing (CN); BEIJING BOE OPTOELECTRONICS TECHNOLOGY CO., LTD., Beijing (CN)

Signed and Sealed this  
Sixth Day of July, 2021

Drew Hirshfeld  
*Performing the Functions and Duties of the*  
*Under Secretary of Commerce for Intellectual Property and*  
*Director of the United States Patent and Trademark Office*